(12) United States Patent
Sadler

(10) Patent No.: US 9,044,007 B2
(45) Date of Patent: Jun. 2, 2015

(54) DEVICE AND METHOD FOR AMBIENT STORAGE OF FRESH/FROZEN TISSUE SECTIONS VIA DESICCATION

(76) Inventor: Theodore R. Sadler, Minneapolis, MN (US)

( * ) Notice: Subject to any disclaimer, the term of this patent is extended or adjusted under 35 U.S.C. 154(b) by 315 days.

(21) Appl. No.: 12/576,168

(22) Filed: Oct. 8, 2009

(65) Prior Publication Data

US 2010/0221830 A1    Sep. 2, 2010

Related U.S. Application Data

(60) Provisional application No. 61/103,750, filed on Oct. 8, 2008.

(51) Int. Cl.
| | |
|---|---|
| *A01N 1/00* | (2006.01) |
| *A01N 1/02* | (2006.01) |
| *B01L 3/00* | (2006.01) |
| *G01N 1/30* | (2006.01) |
| *G01N 1/31* | (2006.01) |

(52) U.S. Cl.
CPC .............. *A01N 1/00* (2013.01); *A01N 1/0273* (2013.01); *A01N 1/0278* (2013.01); *B01L 3/508* (2013.01); *B01L 2300/0809* (2013.01); *B01L 2300/105* (2013.01); *G01N 1/30* (2013.01); *G01N 1/31* (2013.01)

(58) Field of Classification Search
CPC ..... A01N 1/00; A01N 1/0273; A01N 1/0278; B01L 3/508
USPC ........................................ 435/307.1
See application file for complete search history.

(56) References Cited

U.S. PATENT DOCUMENTS

| | | | | |
|---|---|---|---|---|
| 5,409,524 | A * | 4/1995 | Jensvold et al. | 96/8 |
| 6,209,343 | B1 * | 4/2001 | Owen | 62/457.2 |
| 6,231,815 | B1 * | 5/2001 | Bainczyk et al. | 422/550 |
| 6,299,842 | B1 * | 10/2001 | Kozak et al. | 422/550 |
| 2003/0156996 | A1 * | 8/2003 | Delorme | 422/102 |
| 2006/0120945 | A1 * | 6/2006 | Warner et al. | 423/477 |
| 2007/0292959 | A1 * | 12/2007 | Cervi et al. | 436/63 |

\* cited by examiner

*Primary Examiner* — Nathan Bowers
*Assistant Examiner* — Gautam Prakash
(74) *Attorney, Agent, or Firm* — Shewchuk IP Services, LLC; Jeffrey D. Shewchuk

(57) ABSTRACT

The present invention discloses a method for storing and preserving previously sectioned, snap-frozen, and desiccated biological tissue samples at ambient conditions. Also disclosed are devices and systems for ambient storage of biological tissue sections, and methods for forming said devices.

23 Claims, 10 Drawing Sheets

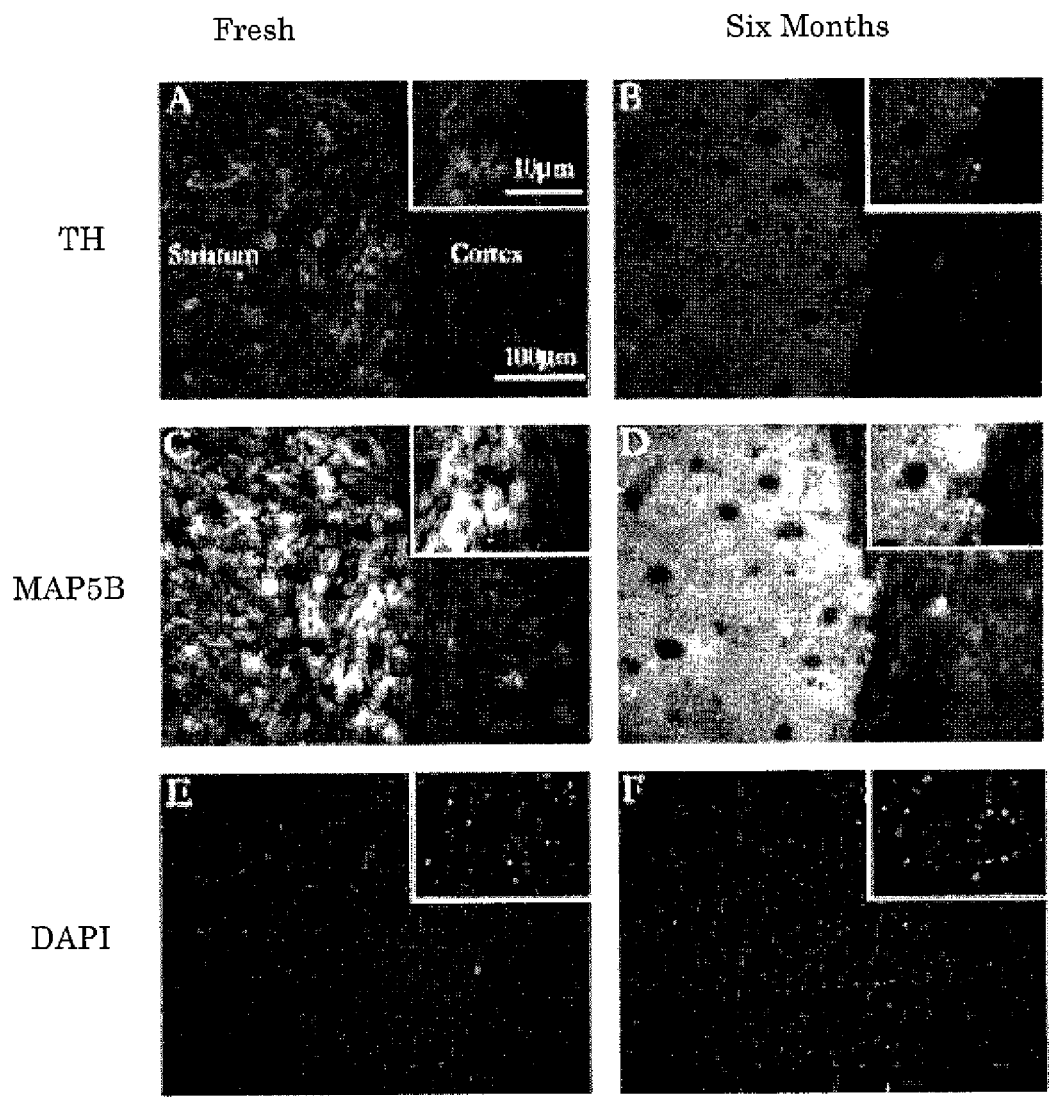
Figure 9A-F

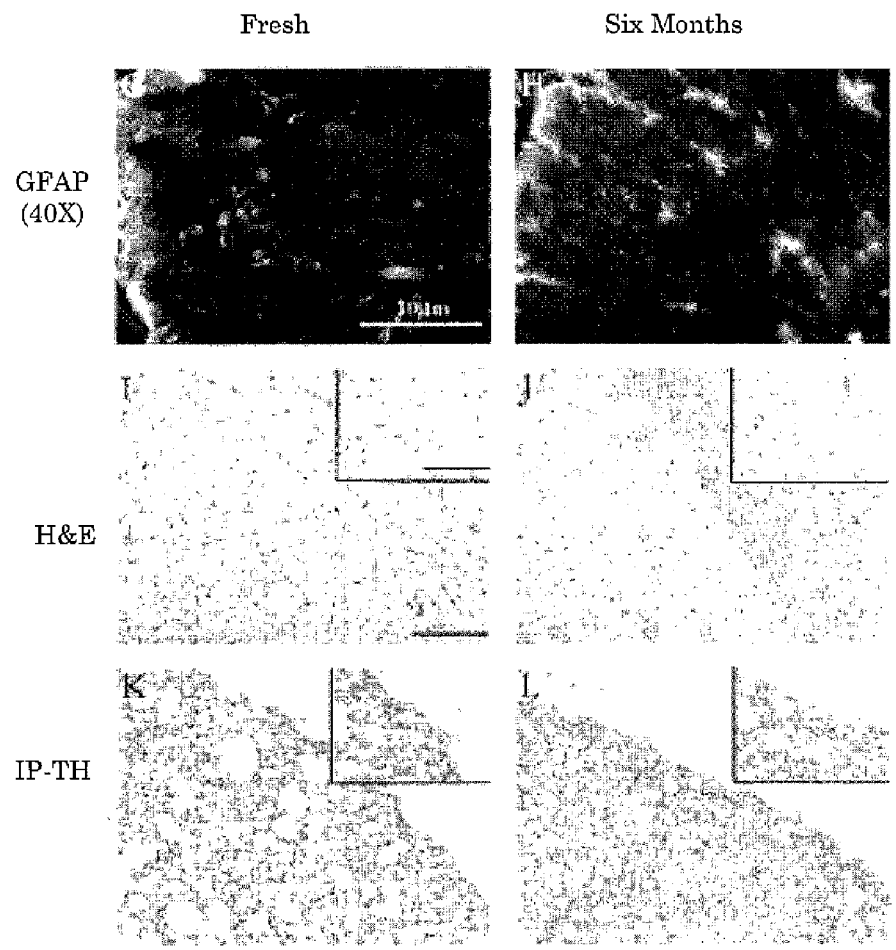
Figure 9 G-L

DEVICE AND METHOD FOR AMBIENT STORAGE OF FRESH/FROZEN TISSUE SECTIONS VIA DESICCATION

CROSS-REFERENCE TO RELATED APPLICATIONS

This application claims the benefit of U.S. Provisional Application No. 61/103,750, filed on Oct. 8, 2008, which application is hereby incorporated herein by reference.

STATEMENT REGARDING FEDERALLY SPONSORED RESEARCH OR DEVELOPMENT

This invention was made with government support under Contract Nos. R24 AT002681 and P30 EY003040 awarded by the National Institutes of Health. The government has certain rights in the invention.

FIELD OF THE INVENTION

The invention pertains to the field of biological sample storage and preservation. More particularly, the invention pertains to methods of preserving biological samples at ambient temperature, as well as systems and devices for implementing the same.

BACKGROUND OF THE INVENTION

Preservation of biological samples is an important task in the workflow of both bench research and clinical applications. Typically, the study design and analysis of ex vivo tissue samples determines the method by which the specimen is processed and preserved. Tissues used for morphological or immunohistochemical analyses are frequently fixed with a common chemical fixative, such as formalin, and are embedded in paraffin. While formalin-fixed paraffin-embedded specimens are well preserved and conveniently stored at ambient room temperatures, the cross-linking and sulfide bond formation caused by the fixative make them less compatible with current molecular techniques (1-3). Hence, epitope retrieval methodologies are used to recover the antigens; but recovery in some instances can be less than optimal (1, 4, 5).

An alternative to the use of fixatives is the century-old method of freezing the tissue at sub-zero temperatures. Freezing the tissue provides a snapshot of the cells as they would appear at the time the sample was removed from the organism, while avoiding degradation of intracellular molecules via autolysis or similar mechanism (6-8). The vox populi among pathologists and histologists is to store snap-frozen tissue (aka fresh/frozen) samples, which have been sectioned and desiccated, at −80° C. Typically, sectioned tissues are placed onto microscope slides (subbed or with electrostatic charge), dehydrated to remove moisture, and immediately stored at cryogenic temperatures.

The widely accepted belief that snap-freezing any tissue adequately preserves protein integrity at cellular and subcellular levels has served as the gold standard for molecular analysis (1-3, 9). Ever since Altmann (7) described cellular degradation in the form of proteolysis, the conventional method of cryogenic storage of frozen tissues has been used, and few deviations from this practice have been reported. However, cryogenic storage of tissue samples is both cumbersome and costly. For example, a recent pilot study conducted at an American university demonstrated that the cost of cryogenic storage can easily run into the range of tens of millions of dollars in operating cost per year, not to mention the large carbon footprint imposed on the environment. In light of the current trend of large scale bio-banking in both clinical and research settings, this cost is likely to grow exponentially.

Therefore, there still exists a need for better methods and devices that will provide cost effective and environmentally friendly ways to store biological samples.

SUMMARY OF THE INVENTION

In light of the above, it is an object of the present invention to provide a solution to the costly problem of tissue sample storage.

This object of the present invention is satisfied by the methods, systems, and devices of the present invention which are based on the unexpected discovery that desiccated biological tissue samples, without the help of chemical preservatives, are capable of being stored at ambient conditions with or without desiccation for at least 6 months without significant degradation. Thus, at the core of this invention is the discovery that valid molecular data can be obtained via Western Blots, Immunohistochemistry, or Chromgen-based staining from previously desiccated biological tissue samples stored at ambient conditions without the use of chemical preservatives. Based on this discovery, the inventor has devised methods, devices, and systems to effectively and economically store and preserve biological samples, obviating the need for cryogenic or chemical preservation techniques.

Accordingly, in a first aspect, the present invention provides a device for storing and preserving a desiccated biological sample at ambient conditions without the use of additional chemical preservatives. A device in accordance with this aspect of the present invention will generally include: a housing configured to accommodate and secure therein one or more desiccated biological tissue samples not containing any preservative; and a desiccating element capable of maintaining a predetermined level of humidity within said housing, wherein said biological tissue samples are desiccated by a physical (although chemical means may also applied). When closed, the housing and the desiccating element form a sealed container not permeable to air and moisture.

In a second aspect, the present invention also provides a desiccating element for use with a storage device as described above. A desiccating element in accordance with this aspect of the present invention will generally include: a container configured to form an air-tight fit with said sample storage device when mounted on the sample storage device to form an air-tight enclosure, wherein said container having one or more compartments containing a desiccant therein, each compartment having an opening formed of an air permeable barrier, and wherein said compartments are configured such that when said container is mounted on the sample storage device, the air permeable barrier openings of the compartments are exposed only to the interior space of the sample storage device.

In a third aspect, the present invention provides a device for storing, preserving, and transporting hygroscopic sensitive materials. Devices in accordance with this aspect of the present invention will generally include an enclosure having defined therein an interior space for storing and securing the hygroscopically sensitive material; and a desiccating element detachably mounted to the enclosure. The enclosure is configured to have an open-state and a closed-state. The interior space of the enclosure can be accessed when the enclosure is placed in its open-state, and is sealed off when the enclosure is placed in a closed-state. The desiccating element generally has a casing having defined therein one or more compartments, each carrying a desiccant therein. The compartments each has barrier that permeable to air and moisture but not the desiccant, and is accessible only to the interior space of the enclosure when the desiccating element is mounted to the enclosure and when the enclosure is closed.

In a fourth aspect, the present invention also provides a method of storing, preserving, and transporting hygroscopically sensitive materials. Methods in accordance with this aspect of the invention generally include the step of placing the hygroscopically sensitive material in a storage device according to third aspect of this invention.

In a fifth aspect, the present invention also provides a system for storing and preserving desiccated biological samples. Systems in accordance with this aspect of the present invention will generally include: one or more storage devices as described above; and a shelving unit for collecting and maintaining said storage devices, wherein said shelving unit is configured to maintain a substantially constant ambient condition.

In a sixth aspect, the present invention also provides a method of storing and preserving a biological tissue sample at ambient conditions without using chemical preservatives. Methods in accordance with this aspect of the invention will generally have the steps of: desiccating the tissue sample with a chemical or physical means; and storing the desiccated tissue sample in a storage device capable of maintaining said tissue sample at a predetermined humidity without applying any chemical preservatives to the tissue sample.

In a seventh aspect, the present invention also provides a method for determining whether a particular biological sample is suitable for storage and preservation by methods of this invention described above. Methods in accordance with this aspect of the invention will generally include the steps of: determining an initial condition of the sample before the storing the sample in the storage device; determining a final condition of the sample after a desired interval; and comparing the final condition to the initial condition of the sample, wherein if the final condition deviates from the initial condition more than a predetermined tolerance, a non-suitable status is indicated for the sample.

In an eighth aspect, the present invention also provides a method of forming a device for storing and preserving biological tissue samples at ambient conditions without using chemical preservatives. Methods in accordance with this aspect of the present invention will generally have the steps of: forming a housing configured for accommodating and securing one or more tissue samples; and forming a desiccating element suitable for use with the housing, wherein: said desiccating element having one or more compartments, each having a desiccant disposed therein, and a side consisting of a air permeable barrier for confining the desiccant to the compartment; and said desiccating element is either formed integrally with the housing or independently as a detachably mounted element.

Other aspects and advantages of the invention will be apparent from the following description and the appended claims.

BRIEF DESCRIPTION OF THE DRAWINGS

FIG. 9 shows photomicrographs of brain tissue sections with hematoxylin and eosin (H&E), immunoperoxidase, or immunofluorescences stains. Using a rat stereotaxtic atlas as a guide, all samples were taken at approximately bregma 0.72 mm (A←P), at a junction between striatum and cortex. (A), (C), and (E) Fresh brain tissue section dual stain against TH and MAP5B, with nuclear counter stain. (B), (D), and (F), Tissue section from 6-month-old desiccated samples with identical stains. (G) Fresh brain GFAP stain. H, GFAP stain of sample after stored in desiccated condition for 6 months. (I) Fresh brain H&E stain. (J) H&E stain of sample after stored in desiccated condition for 6 months. (K) Fresh brain immunoperoxidase stain for TH. (L) immunoperoxidase stain for TH of sample after stored in desiccated condition for 6 months. TH=tyrosine hydroxylase, MAP5B=neuron, GFAP=glia (non-neuronal), DAPI=nuclear stain. Photomicrographs were taken at 2 different magnifications, unless otherwise noted, one at 10× and another at 40× (shown as inset).

DETAILED DESCRIPTION

Having summarized the various aspects of this invention, details of the devices, systems, and methods will now be described with the help of the accompanying drawings and the specific exemplary embodiments below.

1. Storage Devices and Systems

Figure 1:
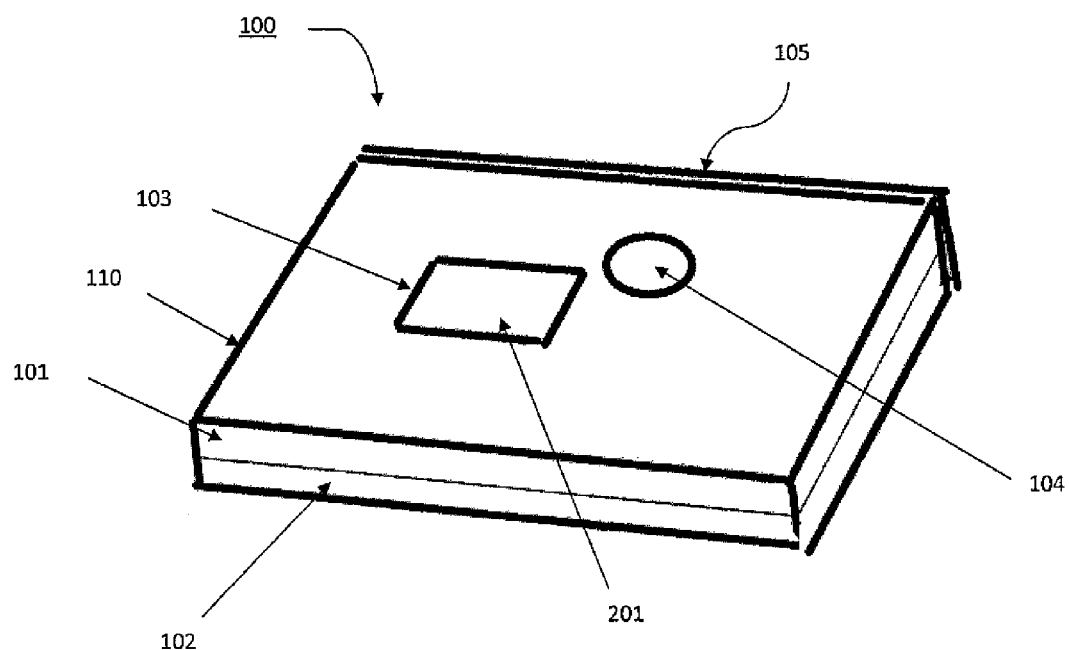
FIG. 1 shows a perspective view of an exemplary storage device in accordance with embodiments of the present invention.

Referring first to FIG. 1, there is shown an exemplary embodiment of a storage device 100 having a housing 110 and a desiccating element 201. The housing is configured to accommodate and secure one or more desiccated biological tissue samples inside its interior space. The desiccating element is capable of maintaining a predetermined humidity within the interior space of the housing. The biological samples are preferably desiccated by a physical means prior to being stored in the storage device. No chemical preservative is applied to the sample or used anywhere in the storage device.

Biological samples suitable for storage by a device of this invention may include brain tissues, muscle (skeletal, smooth, cardiac) tissues, spleen, skin, and/or liver tissues, but are not limited thereto. Other sources of biological samples such as human, animal, plants, fungi, or viral samples may also be storage and preserved by a storage device of this invention.

In a preferred embodiment, the biological samples are snap-frozen prior to being desiccated. The snap-frozen tissues are also preferably sectioned into thin slices. Methods for snap-freezing and sectioning biological tissues are known in the art.

As used herein, the term "desiccation" means the removal of moisture in a biological sample. Numerous methods of desiccation are known in the art, including both chemical and physical methods. The biological samples are preferably desiccated using a physical means because this excludes introducing chemical preservatives, and thereby considerably simplifies the storage and processing requirements. Exemplary physical means of desiccation may include heat drying, freeze drying, microwave drying, vacuum drying, or any other physical drying means known in the art. In a preferred embodiment, simple heat drying is used.

To store the samples in the storage device, the samples may be directly deposited into the container, or may be mounted on other securing elements such as glass microscope slides. Other materials such as graticule slide, plastic, natural components (e.g., formica), or metal may also be used to hold the samples. Accordingly, the housing of the storage device will preferable have suitable securing structures to accommodate the mounting elements. Alternatively, the mounting elements may be integrally formed with the housing. For example, the housing may employ a format similar to the 96-well plates commonly used in the biological art. In such embodiments, the wells are sized such that the biological samples can be easily deposited and secured in the wells.

The size and shape of the housing are not particularly limited. Preferably, they are dimensioned to be easily and efficiently stacked inside a storage shelf unit. Rectangular shaped housing are typically preferred, but other shapes such as squares, hexagons, triangles, and other geometric shapes may also be advantageously used.

The housing may be constructed of any material suitable for the storage requirements of the particular samples. In general, the selected material should be a durable, lightweight, and biologically inert material. The material should also have excellent thermal insulating capabilities, should not be permeable to air or moisture, and should preferably be inexpensive. Other desirable properties may include optical opaqueness in the UV region and shock absorbing capabilities. Exemplary suitable materials may include plastic, glass, wood, metal, fiberglass, Kevlar, or metal alloys, but are not limited thereto.

In general, the desiccating element of this invention removes moisture from inside the housing. During operation, the housing is sealed off to form a closed enclosure with the biological samples securely stored inside. The desiccating element then operates to remove and maintain a predetermined humidity inside the housing. Preferably, a humidity in the range of 0-25% is maintained. More preferably, a humidity of less than 15% is maintained.

Various implementations of the desiccating element may be conceived. For example, it may be integrally formed with the housing, or may be a detachable construct to be mounted onto the housing during use. In a preferred embodiment, a desiccating element of this invention may be a container designed to fit an opening 103 on the housing 110. The fitting should be air tight so that the interior environment of the housing form a substantially closed environment.

Figure 4:
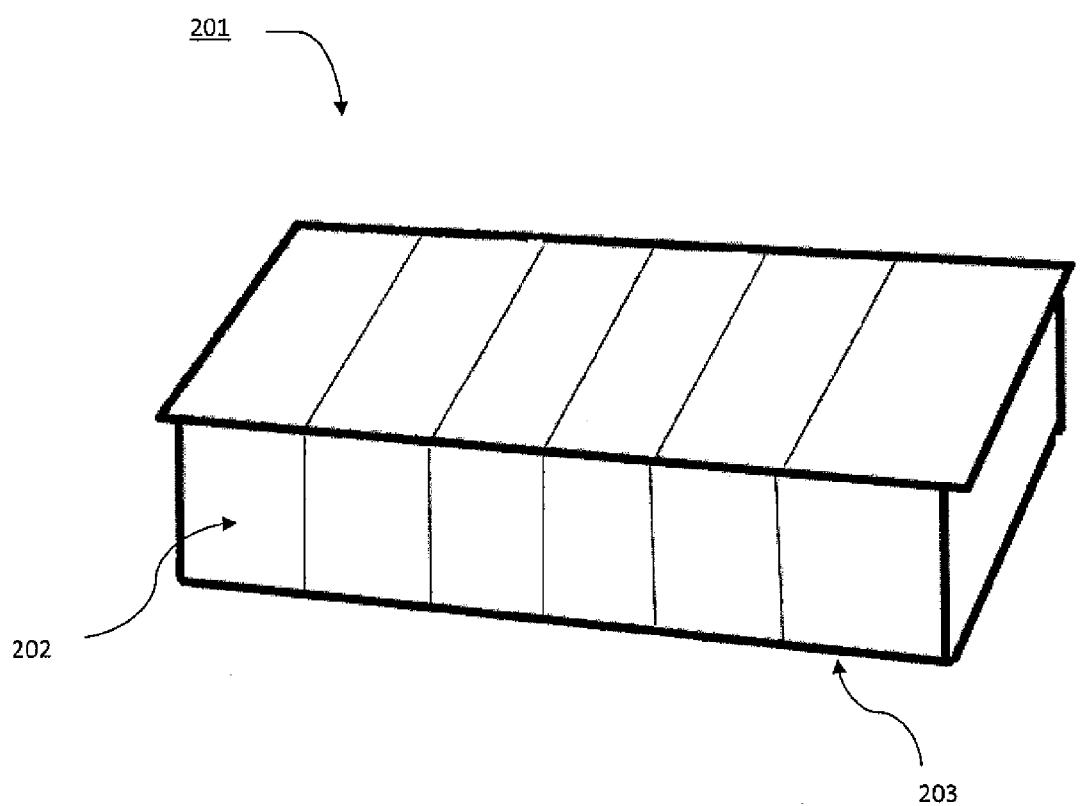
FIG. 4 shows a perspective view of an exemplary desiccant cartridge in accordance with embodiments of the present invention.
Figure 5:
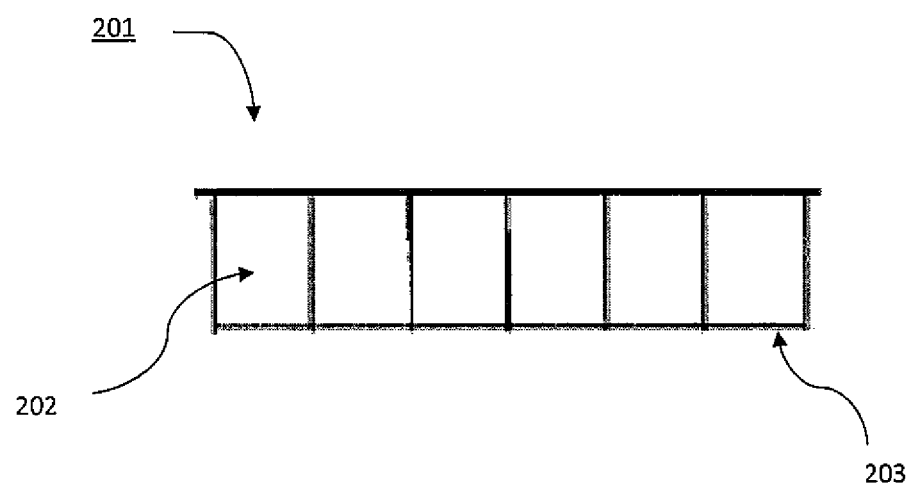
FIG. 5 shows a side view of an exemplary desiccant cartridge in accordance with embodiments of the present invention.

FIG. 4 shows an exemplary desiccating element in the form of a cartridge. FIG. 5 shows a side view of the same desiccating cartridge. As shown in the figures, the exemplary desiccating cartridge 201 has a container having a plurality of compartments 202 (note that in some embodiments, a single compartment configuration can also be used). The container housing is made of a material that is not permeable to air or moisture. Desiccants are disposed inside of compartments 202 before use. One side of each of the compartments has an air permeable barrier 203 that is only permeable to air and moisture, but not the desiccant. In a preferred embodiment, the barrier may be constructed with an one-way hydrophobic membrane such as Desiccants are generally selected based on the desired humidity and duration, as well as chemical, compatibility. Numerous suitable desiccants are known in the art. Examples may include organic desiccants (e.g. rice), and minerals (e.g. drierite, silica gel, calcium sulfate, calcium chloride, montmorillonite clay, and cobalt chloride), but are not limited thereto.

Figure 2:
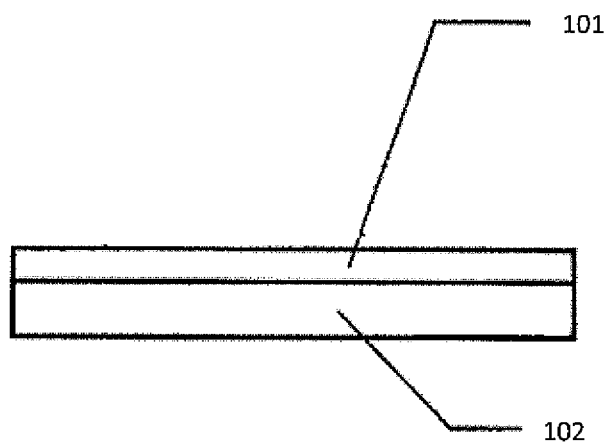
FIG. 2 shows the front side view of an exemplary device in accordance with embodiments of the present invention.
Figure 3:
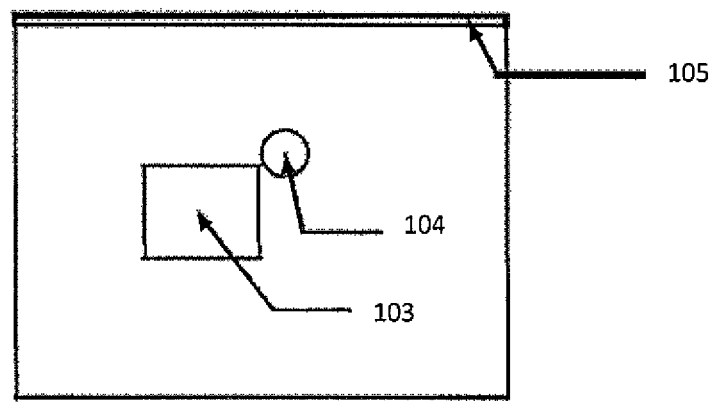
FIG. 3 shows the top view of an exemplary device in accordance with embodiments of the present invention.

To allow loading and unloading of the samples, the housing should be constructed so that the interior space may be accessed in an open state while loading and unloading the sample, and be sealed off in a closed state when storing the sample. In a preferred embodiment, the housing is constructed in the form of a hinged box. Referring again to FIG. 1, in this exemplary embodiment, the housing is made of a top-half component 101 and a bottom-half component 102, linked together by a hinge 105, living or otherwise. The two halves are then locked together by clasps on the front (opposite to the hinge) The bottom-half is configured to accommodate the biological samples or the mounting elements. The top-half is configured to receive the desiccating cartridge 201 at the opening 103. The housing may be opened and closed by moving the two half-components about a hinge. When closed, the two half-components form a sealed enclosure. FIG. 2 shows the device housing in its closed state viewed from the front side. FIG. 3 shows the device housing viewed from the top side.

To monitor the environmental conditions of the storage device, additional environmental sensing elements may be incorporated. Referring again to FIG. 1 and FIG. 3, a sensing element 104 is shown as being incorporated on the top side of the device housing. The sensing element may include any sensing elements commonly known in the art. For example, a hygrometer may be incorporated to monitor the humidity inside the housing. Other sensing devices such as temperature sensor, pressure sensor, UV sensor, accelerometer, or any other types of environmental sensors.

While the above described storage device was conceived initially to accommodate biological samples, it will be appreciated by those skilled in the art that the novel and simplistic design of the above described device also makes it particularly advantageous in applications where a portable and reusable low humidity-environment storage device is required. Therefore, in one aspect, this invention provides a portable, reusable, inexpensive, and easy to maintain low humidity storage device for storing and transporting humidity sensitive contents.

Some example of contents that may be stored and transported by a device of this invention may include pure alkali metals or other hydroscopically reactive compounds; diagnostic biologics or medicines (e.g. DNA, RNA, or antibodies); hydroscopically sensitive electronic components (e.g. biochips or neurochips); archeological samples (e.g. ancient samples from Egyptian tomes, or paleontological samples); archival documents (e.g. rare books, historical documents, films, etc.); fuel-cell components (e.g. biological fuel cell components such as myocytes of the electric eel, or chlorophyll for organic batteries); hydroscopically sensitive minerals or salts, and space-bound astrobiological samples.

One particularly interesting non-biological application is that of storing and transporting of pure alkali metals. In recent year, green energy technologies have been developed in which pure sodium is melted by solar energy and the molten sodium is used to heat water which in turn generates steam for power generation. However, storage and transportation of sodium metals currently employs oil infusion. If this process becomes more common place the mass quantity of oil infused sodium metal could be a safety (slippage) hazard as well as an additional fire hazard (oil storage and disposal). Devices of this invention may be advantageously used to provide a more ideal storage solution without the need to use a petroleum product.

In practice, a user may use several storage devices at the same time to store a great number of samples. Accordingly, a convenient method of identifying the content of each storage device is desired. Thus, in a preferred embodiment, devices of this invention may further include a sample identification element to facilitate identification In addition to identifying the content of the storage, it is also important to know how long a sample has been stored in the storage. Therefore, in another preferred embodiment, the storage device may further include a time indicator for indicating a temporal information relating to the content of the sample. There are also numerous possibilities for implementing the time indicator. For example, a simple sticker label with handwritten dates may serve the purpose. Other implementations may include a digital timer, and dial indicator, or any other commonly used time indicating mechanisms.

One recent growth area of biological sample storage is bio-banking. In such applications, massive amount of biological samples are collected, processed, and then archived to await further use or analysis. When more than one storage device is involved, an organized way of managing the plurality of the storage devices become important to an efficient workflow. Thus, the present invention also provides systems for efficiently managing and maintaining the storage devices.

Several large scale bio-banking systems have been commercialized, including those with robotic manipulators. However, current systems generally rely on cryogenic or chemical techniques for sample storage and preservation. Therefore, such systems tend to be complex and expensive, suitable only for well-funded institutions. For field research in rural or undeveloped areas, such approach would be impossible, or at least impractical.

In contrast, storage devices of this invention do not require any chemical preservative or cryogenic treatment. Samples are stored at normal ambient laboratory conditions, requiring no special attention for maintenance or upkeep. The flexible form-factor requirements of the device housing also renders them easily compatible with existing hardware and infrastructures. For example, storage device of this invention may be made to have dimensions approximating the commonly used 96-well plates, thus, making them immediately usable with robotic systems that are originally designed to work with the plates. In such cases, using the storage devices of this invention will yield substantial savings as the original system may be operated without cryogenic refrigeration or other associated operating expenses.

Accordingly, systems in accordance with embodiments of this invention will generally include one or more storage devices as described above, and a shelving unit for collecting and maintaining the storage devices. The shelving unit is preferable one that is capable of maintaining a substantially constant ambient condition. In some further embodiments, the systems may further incorporate robotic manipulators for conveying the storage units.

2. Methods for Storing, Preserving, and Transporting Biological Samples

In general, methods for storing, preserving and preserving a biological tissue sample in accordance with embodiments of the present invention will include the steps of desiccating the tissue sample with a physical means; and storing the desiccated tissue sample in a storage device capable of maintaining said tissue sample at a predetermined humidity without applying any chemical preservatives to the tissue sample.

Suitable storage devices and physical means of desiccating the tissue samples are as described above.

Biological samples that may be stored in this manner may include brain tissues, muscle (skeletal, smooth, or cardiac) tissues, spleen tissues, skin, or liver tissues, but are not limited thereto.

In some preferred embodiments, a step of snap-freezing biological tissue sample may be performed prior to desiccating the samples. Sectioning the biological tissue sample into individual sections may also be performed following snap-freezing of the samples.

Procedures of sectioning and preparing a biological sample suitable for storage is generally known in the art. An exemplary procedure is also provided in the Experiment section below.

Although storage methods of this invention is applicable generally, occasionally, there may be a need to verify the suitably of the method for a particular experiment. Accordingly, in one aspect, the present invention also provides a method for determining a sample's suitability for being stored and preserved using the storage method described above.

Methods in accordance with this aspect of the invention will generally have the steps of determining an initial condition of the sample before storing the sample in the storage device; determining a final condition of the sample after a desired interval; and comparing the final condition to the initial condition of the sample, wherein if the final condition deviates from the initial condition more than a predetermined tolerance, a non-suitable status is indicated for the sample.

3. Methods for Storing, Preserving, and Transporting Hygroscopically Sensitive Materials As mentioned previously, devices of this invention also find general applications in the storage and transportation of hygroscopically sensitive materials. Accordingly, in one aspect, this invention also provides methods for storing, preserving, and transporting hygroscopically sensitive material utilizing devices of this invention.

In general, a method according to this aspect of the invention will include the steps of: placing a hygroscopically sensitive material in a storage device of this invention. It will be understood that samples stored in each device may be of different types, so long as they are properly separated.

4. Methods for Making the Storage Devices

While the above described methods, devices, and systems significantly improve the efficiency of the typical workflow in a lab and brings substantial savings to the end users both in terms of money and time, the present invention also makes a significant contribution to the suppliers of storage systems and devices by way of providing a new product category which in turn makes available previously unviable business models and previously unconcealed manufacturing methods.

Accordingly, in one aspect of the present invention, there is provided a method of making a device for storing and preserving biological tissue samples at ambient conditions. In one embodiment, the method includes the steps of forming a housing configured for accommodating and securing one or more tissue samples; and forming a desiccating element suitable for use with the housing. The desiccating element has one or more compartments, each having a desiccant disposed therein. Each of the compartments also has a side consisting of an air permeable barrier for confining the desiccant to the compartment while still allowing air to be in contact with the desiccant. The desiccating element may be either formed integrally with the housing or independently as a detachably mounted element.

In a preferred embodiment, the method further comprises a step of forming a top-half component and a bottom-half component. The bottom-half component is configured to accommodate one or more tissue storage elements, each having a snap-frozen desiccated tissue section disposed thereon. The two components are, configured such that they are capable of combining together to form a closed container to enclose the tissue storage elements so as to provide and maintain a substantially constant ambient condition for the tissue storage elements. The top-half may further comprise an opening configured to fit a desiccating element, which may be in the form of a cartridge containing desiccants. The desiccating element is generally detachably mounted to the top-half component, forming an air-tight seal with the opening when mounted. The top-half component may further incorporate an environmental sensor such as a hygrometer. The two components may be combined via a "living hinge" component.

Advantages for using the devices, systems, and methods of this invention are many fold. Some examples include the reduction and/or elimination of the use of harmful or toxic chemicals typically employed to fix tissue samples for assays and a reduction of energy demanding storage units (e.g., freezers). A storage device of this invention will only require normal shelf space and replacement of its desiccating element (e.g. desiccant cartridge) when necessary.

To further illustrate the present invention, the following specific embodiment and experiment are provided.

EXAMPLE

In a preferred embodiment, a storage device of the invention would consist of three plastic molded parts, fabricated by injection or, CNC (computer numerical controlled machine tool), which provides a lower overhead/cost to market than injection molding (see FIGS. 1-5):

The bottom half (~235 mm long, 120 mm wide, and 21 mm high with a wall thickness of ~4 mm, of which a 1 mm centered-groove [1 mm×1 mm] would inscribe the top rim to hold a silicone rubber o-ring) that would hold the microscope slide vertical along its shortest side in three rows—each row would be approximately 6 mm in length. Each column of rows would hold approximately 45 slides for a total capacity of 135 slides. The floor of the container would contain a soft material (e.g., cork or silastic) to prevent damage.

The top half would have the same dimension as described above with an opening in the middle of the approximately 75 mm by 50 mm. Both the top and bottom half would be formed with a conventional hinge or "living hinge" between the two components to assist in closing the container appropriate and a push button locking mechanism to secure the two halves. The container would be locked together with clasps when closed. Also, in the upper corner of the top portion would be a 10 mm diameter hole to secure a hygrometer that will indicate the appropriate moisture content inside the container.

The replaceable desiccant cartridge makes up the third part that would snap-fit into the opening of the top of the container. This portion would be approximately 7×3 mm with a depth of 1.5 mm. This cartridge would have a simple cage for support and a one-way hydrophobic membrane such as polyethersulfone, nylon, polytetrafluoroethylene, ultrasonically welded onto the cage after the cartridge is filled with desiccant.

Experiment

The following experiment illustrate the unexpected discovery upon which the various methods, devices, and systems of the present invention depend.

Material and Methods

Tissue Acquisition

Brain tissue was harvested from rats (n=5) immediately after intravenous euthanasia (1.0 mL Euthasol I.C., Delmarva Laboratories Inc, Greenland, N.H.). Tissues were snap-frozen at $-55°$ C. in methylbutane cooled with dry ice. The tissue samples were submerged in the cryogenic solution for 14 seconds, removed, and embedded in optimal cutting temperature (OCT) solution (Sakura Finetek, Torrance, Calif.). Brains were sectioned (Microm HM550 microtome/cryostat, Microm International, Walldorf, Germany) at 20 µm (used for protein extraction) and 10 µm (used for tissue staining) at $-18°$ C. Three consecutive sections were placed onto electrostatic-charged microscope slides (Superfrost, VWR Scientific, West Chester, Pa.), and the slides were either dried on a microscope slide warmer (Lablyne, Melrose Park, Ill.) at $50°$ C. for 45 minutes (noted as "With Heat," or "w/h") or merely air dried at room temperature for 15 minutes (noted as "Without Heat," or "wo/h"). Samples were tested after being stored at the following conditions: frozen ($-80°$ C.), ambient ($20°$ C. and 45% relative humidity), and desiccated ($20°$ C. and <10% relative humidity) for 1 day, 1 week, 1 month, and 6 months. The assay matrix is summarized in Table 1, where all tests were performed in triplicate.

Tissue Preparation

Samples of tissue sections (20 µm) were excised under a dissecting microscope (Olympus, Tokyo, Japan) with a disposable 1.0 mL syringe and 27 G ½" needle (Becton Dickinson Co, Franklin Lakes, N.J.). Specifically, the area of tissue to be removed (ie, striatum) was outlined with the needle, then a minute quantity of protein extraction buffer (PEB, T-PER, Pierce Biotechnology Inc, Rockford, Ill.) was pipetted (Finnpipette, ThermoScientific, Waltham, Mass.) in 2.0 mL increments on the outlined section until the buffer immersed approximately half of the inscribed area. To both minimize tissue loss and ease transfer into a microcentrifuge tube (USA Scientific Inc, Ocala, Fla.), the tissue was removed from the slide using the 27 G needle and combined with PEB. The tissue/PEB was carefully transferred to a 1.5 mL tube.

Approximately, 150 mL of PEB without protease inhibitors was added to the semi-dried sample, and the tube was placed on ice. Immediately after sample preparation, the protein was extracted.

Protein Extraction

To minimize sample loss, the same 270 needle used to excise the tissue was used to aspirate the mixture 10 times, while cautiously avoiding introduction of excess air in the mixing process. This series was repeated using a 30 G needle (Becton Dickinson Co) with the same syringe. The sample was agitated (Maxi Mix, Barnstead International, Dubuque, Iowa) for 60 seconds, and then centrifuged (Eppendorf model 5415C, Hamburg, Germany) for 10 minutes at 10,000 G at room temperature (201 C). The supernatant was transferred into a clean microfuge tube, and the pellet was stored at 201 C. Supernatant total protein concentration was quantified with a microplate reader (Benchmark Plus, Bio-Rad Inc, Hercules, Calif.), via the Bradford method (minimal protein detection size of 4.5 kd), and normalized by area removed.

Silver Stain

Protein samples (total loading mass=10.0 μg) were resolved by sodium dodecyl sulfate-polyacrylamide gel electrophoresis on a 10% Tris-HCl gel (Bio-Rad Inc) at constant voltage (120 V) for approximately 45 minutes. The gel was silver stained, dried overnight using a commercial gel drying kit (Owl Inc, Portsmouth, N.H.), and imaged with a conventional flatbed scanner at 600 dpi on the following day.

Western Blot

Protein samples were resolved by sodium dodecyl sulfate-polyacrylamide gel electrophoresis on a 10% Tris-HCl gel at constant voltage (120 V) for approximately 45 minutes. Proteins were transferred onto a PVDF membrane (Bio-Rad Inc) overnight at 40 volts and 41 C. A 5% nonfat milk (NFM) blocking solution (Bio-Rad Inc) containing Tris-buffered saline with 0.01% Tween-20 (TBS-T) was applied to the membranes for 60 minutes at room temperature.

The membranes were subsequently washed 3 times, for 5 minutes each in TBS-T. The membranes were then examined for tyrosine hydroxylase (TH) activity with a mouse anti-rat monoclonal antibody (Chemicon Inc, Temecula, Calif.) in a 5% NFM/TBS blocking solution (1:1000) overnight at 41 C with mild agitation (Orbit Shaker, Barnstead International). To normalize sample loading, the ubiquitous enzyme, glyceraldehyde-3-phosphate dehydrogenase (GAPDH, Chemicon Inc) blot was performed. Briefly, the membranes were incubated in mouse anti-rat GAPDH and 5% NFM/TBS-T at a 1:300 dilution overnight at 41 C with mild agitation. Expression of both TH and GAPDH was detected with 1:10,000 and 1:5000 dilution horseradish peroxidase-conjugated secondary antibody (Vector Laboratories Inc, Burlingame, Calif.) and chemiluminescent solution (Super Signal West Pico, Pierce Biotechnology Inc, Rockford, Ill.) following the manufacturer's instructions.

Hematoxylin and Eosin Stain

OCT-embedded, fresh, and archived brain sections were fixed in acetone and stained with hematoxylin and eosin.

Immunoperoxidase Stains

OCT-embedded, fresh, and archived brain sections were fixed with 4% paraformaldehyde for 15 minutes, and washed twice for 5 minutes in phosphate-buffered saline (PBS) with Tween-20 (PBS-T) washing solution. To block endogenous peroxidases, samples were incubated in 0.1% $H_2O_2$ in 1 PBS for 20 minutes at room temperature.

After blocking for 60 minutes with serum blocking solution (10% normal goat serum and 1% bovine serum albumin in 1 PBS), the sections were incubated overnight at 4° C. with TH diluted at 1:500 in 1 PBS. Samples were then washed 3 times for 5 minutes each in 1 PBS, and incubated with a secondary antibody, Biotinylated Anti-Mouse (Vector Laboratories Inc, 1:100) for 30 minutes at room temperature. While the secondary antibody incubated, the avidin-biotinylatedperoxidase complex solution was prepared and stored at 4° C. for 30 minutes before use. The secondary antibody was washed off with 1 PBS 3 times for 5 minutes each, and subsequently incubated with avidin-biotinylatedperoxidase complex solution for an additional 30 minutes at room temperature.

After a wash with 1 PBS, a solution of 3-amino-9-ethylcarbazole was applied to the samples for a maximum of 6 minutes, or until red reaction product developed. The reaction was terminated by a 1 PBS wash. Finally, samples were counterstained with hematoxylin and mounted with aquamount and cover-slipped.

Immunofluorescent Stains

Brain tissue samples were either dual-labeled (fluorescent) with TH and MAP5B or labeled individually for GFAP with a 4',6-diamidino-2-phenylindole (DAPI) counterstain to evaluate epitope recognition. OCT-embedded brain sections (fresh and archived) were fixed with 4% paraformaldehyde for 15 minutes, and washed twice in PBS-T washing solution for 5 minutes. After blocking for 60 minutes with serum blocking solution (10% normal goat serum and 1% bovine serum albumin in 1 PBS), the sections were incubated overnight at 4° C. with TH diluted at 1:500 in 1 PBS. Next, the sections were treated with horse anti-mouse Rhodamine red (Vector Laboratories Inc) secondary antibody (diluted 1:40 in PBS) for 60 minutes. After 3 PBS-T rinses, the tissues were blocked for 120 minutes with serum blocking solution (10% normal goat serum and 1% bovine serum albumin in 1 PBS), and incubated overnight at 4° C. with MAP5B (a stable structural protein found in neurons) diluted at 1:500 in 1 PBS. Next, they were treated with horse anti-mouse FITC (Vector Laboratories Inc) secondary antibody (diluted 1:40 in PBS) for 60 minutes. Samples tested for GFAP (stable structural protein found in glial, non-neuronal cells) activity were treated similarly, where samples were fixed, rinsed, and blocked as noted above and then incubated overnight at 4° C. diluted at 1:500 in 1 PBS. GFAP samples were treated with horse anti-mouse FITC (Vector Laboratories Inc) secondary antibody (diluted 1:40 in PBS) for 60 minutes. The signal was detected with DAPI fluorescent mounting media (Vector Shield, Vector Laboratories Inc). Images were acquired with a Zeiss LSM-510 laser scanning confocal microscope (Carl Zeiss, Thornwood, N.Y.) using a plan-neofluar 40 oil immersion lens, NA 1.3, Slides were scanned under the same conditions for magnification, laser intensity, brightness, gain, and pinhole size. Images were processed using the LSM 510 software version 3.2 SP2.

Results

Figure 6:
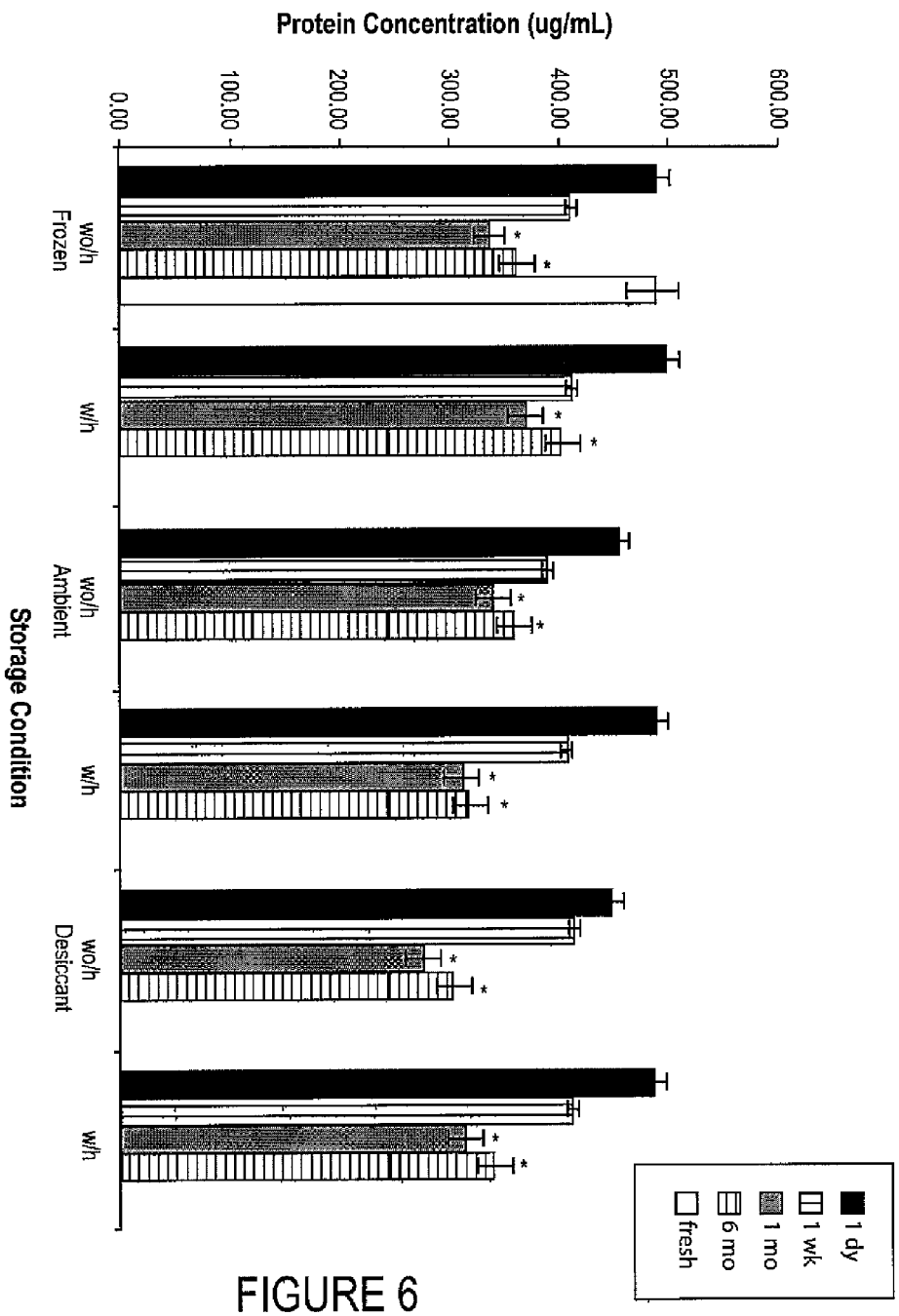
FIG. 6 shows a comparison of normalized protein concentrations (µg/mL) extracted from 20 µm murine brain tissue sections stored at various conditions over a 6-month period. Frozen refers to tissue sections stored at −80° C., ambient refers to sections stored at room temperature (RT, ~22° C.), and desiccated refers to sections stored at RT with low RH. Slides that were not placed on a slide warmer are noted as "wo/h" and those that were are noted as "w/h". Error bars represent ±SEM. Statistically significantly difference, $P<0.05$ (Student t test), represented by *. RH indicates relative humidity; w/h, with heat; wo/h, without heat.

Protein extraction is possible from brain tissue sections after 6 months without cryogenic storage or chemical fixatives. Tissue sections stored with or without desiccant at ambient temperatures provide protein concentrations comparable to fresh samples after 6 months (FIG. 6), though ambient and desiccated samples provided statistically and significantly less protein per given volume as calculated against a normalized region removed. This reduction in protein concentration can be attributed to the technical difficulty in isolating tissues from the slide by hand, which resulted in minor loss of sample. Specifically, some pieces of the ambient and desiccated tissue sections possessed an electrostatic charge that at times were repelled off the needle tip by the minor electrostatic charge on the plastic microcentrifuge tube.

Figure 7:
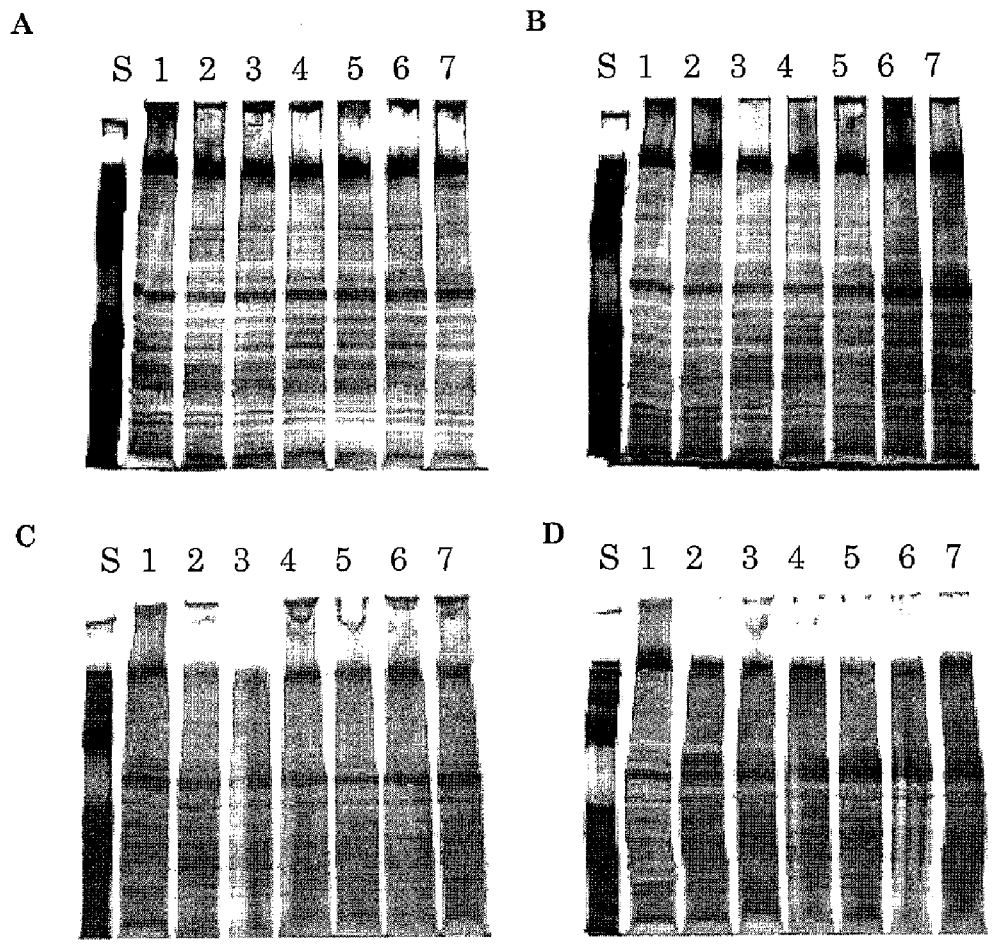
FIG. 7 shows an examination of protein degradation from 20 µm brain tissue sections at defined time points from various storage conditions. Extracted samples were resolved on a denaturing gel and stained with silver method. (A) One-day-old samples. (B) One-week-old samples. (C) One-month-old samples. (D) Six-month-old sample. S=Protein calibration standard. 1=Fresh brain tissue section. 2=Frozen brain tissue section (without heat). 3=Ambient brain tissue section (without heat). 4=Desiccated brain tissue section (without heat). 5=Frozen brain tissue section (with heat). 6=Ambient brain tissue section (with heat). 7=Desiccated brain tissue section (with heat).

Proteins from tissues stored at ambient conditions after 6 months, particularly those desiccated, are similar to both fresh and frozen samples. Silver stain images from 1-day-old, 1-week-old, and 1-month-old brain sections stored at ambient conditions are almost indistinguishable from their fresh or frozen counterparts as they exhibit similar appearances in fractionation patterns while displaying the least change in band definition (FIG. 7). The most observable change in band profile was detected with the 6-month-old specimens, which displayed only a minor loss in band resolution as compared with fresh and frozen samples. Overall, sample bands appear sharp with minimal blurring, uncharacteristic of tissue that is undergoing proteolysis or complete degradation. These observations appear congruent with the results shown in FIG. 6, demonstrating relatively identical protein detection and concentration over time at various storage conditions.

Figure 8:
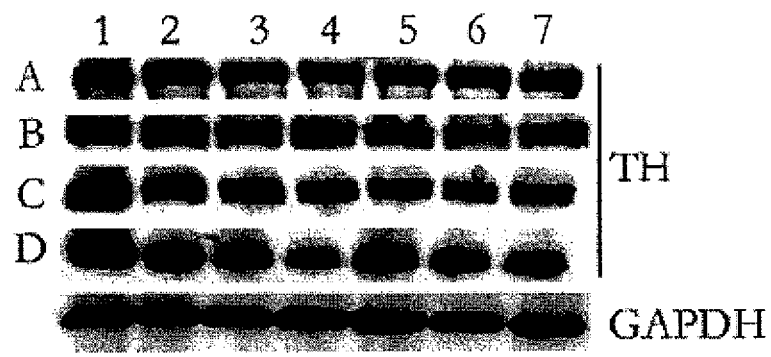
FIG. 8 shows a demonstration of epitope detection of target protein extracted from 20 µm brain tissue sections at defined time points from various storage conditions. Samples were resolved on a denaturing gel and Western blot performed for tyrosine hydroxylase (TH). GAPDH served as internal loading control, 1-month samples shown is representative. (A) One-day-old sample. (B) One-week-old sample. (C) One-month-old sample. (D) Six-month-old sample. 1=Fresh brain tissue section, 2=Frozen brain tissue section (without heat). 3=Ambient brain tissue section (without heat). 4=Desiccated brain tissue section (without heat). 5=Frozen brain tissue section (with heat). 6=Ambient brain tissue section (with heat). 7=Desiccated brain tissue section (with heat). GAPDH indicates glyceraldehyde-3-phosphate dehydrogenase.

Epitopes from tissue that have been desiccating for over 6 months are comparable to fresh and frozen samples. All brain tissue sections display equal levels of TH over time (FIG. 8). Two bands were identified as possible rat-specific isoforms of TH. Furthermore, equal loading between all samples was verified by GAPDH detection.

Immunoflorescent stains for TH and MAP5B or GFAP proteins remain unchanged across various aged brain sections. Immunoperoxidase stains were equally readily identifiable, and displayed minimal differences between fresh and desiccated samples.

Hematoxylin and eosin stains display minimal changes after 6 months as well. Dual TH and MAP5B or GFAP staining was readily detectable after 6 months desiccation compared with fresh sample (FIGS. 9A-H). Here, even astrocytic processes were easily seen after 6 months of desiccated storage. A negative control slide (only secondary antibodies added) displayed no activity (data not shown). After 6 months, eosin staining was reduced compared with fresh sample, yet basophilic structures, in particular, the cell nucleus had comparable hematoxylin staining. Additionally, nuclear morphology appeared consistent between samples (FIGS. 9I, J). Similarly observed with immunofluorescent stains, immunoperoxidase staining revealed little change (FIGS. 9K, L).

Discussion

Concentration of protein from the various samples, though calculated to be statistically different between ambient and desiccated samples, may not have reached a statistically significant difference if the tissue collection processes did not prove to be as difficult. Dissimilarity in calculated protein concentration notwithstanding, the integrity of proteins extracted from brain tissue sections stored at ambient condition stored with or without desiccant tissues over 6 months appeared similar to fresh and frozen samples as evidenced by the silver stain, a method understood to be more sensitive than Coomassie. Minor loss of definition was observed after a month of storage, yet desiccation at room temperature was well defined and comparable to either fresh or frozen samples. Only, after 6 months of storage at ambient temperatures was degradation evident, yet if products of complete proteolysis had been present, the lane in question would have displayed a smear, which it did not.

Western blot analysis was performed to determine whether the epitopes of interest remained recognizable. An enzyme was selected as the protein of interest because enzymes are known to be potentially sensitive to decomposition or degradation at ambient conditions, that is, room temperature. The chosen epitope target was TH, a critical enzyme with various levels of activity present in all catecholaminergic cells, especially in tissues that react to the sympathetic response, such as brain, heart, and kidneys. Additionally, it is worth noting that the different molecular weight bands observed for TH can be explained by the recent evidence that 2 isoforms of TH exist in the rat whereas only 1 isoform is known to be produced in subprimate species. To normalize sample loading, the membranes were blotted for GAPDH, a ubiquitous housekeeping protein found in almost all tissues. Additionally, signal intensities of all tissues from fresh to 6 months appear equivalent, with no detectable loss from archived specimens.

Immunofluorescent results demonstrated no difference in signal intensity over time. Both MAP5B and TH stains/signals counterstained with DAPI remained consistent, as well as easily recognizable. As compared with fresh samples, astrocytic processes of GFAP-stained specimens were clearly identifiable even after 6 months desiccation. Although not intending to be bound by any particular theory, the following explanation is offered to explain why the investigated proteins from heat-dried, snap-frozen tissue sections stored at ambient condition, in particular the desiccated ones, do not appear degraded and epitopes of interest remain detectable: First, proteosome-based degradation is interrupted, where either the prolonged exposure to 50° C. or air-drying for 15 minutes may have potentially affected the ability of proteosome/ubiquitin complex to efficiently degrade proteins, instead of mere denaturation. Second, cellular desiccation due to a combination of prolonged elevated temperatures and thin tissue section impedes cellular processes, including action of degradative enzymes. Third, a combination of attenuated degradative process and the absence of water have altered the functional structures of various enzymes, which typically produce irreversible damage. Fourth, proteins in general, may simply be more stable at ambient conditions than they have been previously perceived.

From the present experimental results, several conclusions can be drawn that appear to contradict the central dogma of snap-frozen heat-dried tissue section storage. First, it is possible to extract proteins from brain tissue section with minor indication of degradation after 6 months, as evidenced by silver stains, there exist significant benefit by storing tissue samples with desiccant at ambient conditions without concern for loss of molecular data. Next, the investigated epitopes (TH, MAP5B, GFAP, and GAPDH) were successfully detectable in the target tissues as shown by immunofluorescence, immunoperoxidase, and Western blots. Thus, it has been demonstrated herein that snap-frozen heat-dried tissue sections may be stored at ambient, desiccated conditions for up to 6 months at minimum without significant damage to protein integrity.

While general applicability is assumed for the present invention, those skilled in the art will readily recognize that certain proteins may fall outside of this norm due to their variable stabilities. However, such instances may be readily identified with a routine test to verify the suitability of this method and shall not subtract from the general applicability of the present invention.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

References

The following references are each relied upon and incorporated herein by reference:
1. Chu W S, Liang Q, Liu J, et al. A nondestructive molecule extraction method allowing morphological and molecular analyses using a single tissue section. Lab Invest 2005, 85(11):1416-28.
2. Perlmutter M A, Best C J, Gillespie J W, et al. Comparison of snap freezing versus ethanol fixation for gene expression profiling of tissue specimens. J Mol Diagn 2004, 6(4):371-7.
3. Gillespie J W, Best C J, Bichsel V E, et al. Evaluation of non-formalin tissue fixation for molecular profiling studies. Am J Pathol 2002, 160(2):449-57.
4. Shi S R, Key M E, Kalra K L. Antigen retrieval in formalin-fixed, paraffin-embedded tissues: an enhancement method for immunohistochemical staining based on microwave oven heating of tissue sections. J Histochem Cytochem 1991, 39(6):741-8.
5. Shi S R, Cote R J, Taylor C R. Antigen retrieval techniques: current perspectives. J Histochem Cytochem 2001, 49(8): 931-7.
6. Harris R J. Preservation of biological materials by freeze-drying. Nature 1951, 168(4281):851-3.
7. Altmann R. Die Elementarorganism und ihre Beziehungen Zu den Zellen (The elementary organism and their relations with the cells). Leipzig: Verlag Von Veit & Comp; 1894.
8. Boe J, Greaves R I. Observations on the biological properties of B.C.G. treated by freezedrying. Acta Tuberc Scand 1950, 24(1-2):38-46.
9. Hershko A, Ciechanover A. Mechanisms of intracellular protein breakdown. Annu Rev Biochem 1982, 51:335-64.

What is claimed is:

1. A storage device for storing and preserving biological samples, comprising:
a housing comprising at least two housing portions which jointly define an interior space adapted to accommodate and secure therein a plurality of biological samples, the two housing portions being openable with respect to each other to permit access to the interior space, the two housing portions being closeable with respect to each other in a sealed fashion, the two housing portions being each formed of a material which is not permeable to air or moisture, one of the two housing portions in the closed state defining a cartridge opening; and
a desiccating cartridge formed of a material which is not permeable to air or moisture, the desiccating cartridge being sized and shaped to fit and be removably received in the cartridge opening forming an air-tight fit with the housing so that, when the housing portions are in the closed state, the desiccating cartridge and the housing jointly seal the interior space of the housing off from the exterior environment, the desiccating cartridge having a compartment containing desiccant therein, the desiccating cartridge having one side facing the interior space through the cartridge opening, which one side is permeable to air and moisture but not permeable to the desiccant; and
a one way hydrophobic membrane disposed between the interior space and the desiccant when the cartridge is received in the cartridge opening and the housing portions are in the closed state.

2. The storage device of claim 1, wherein the housing further comprises a plurality of sample mounting elements for mounting and securing the plurality of desiccated biological tissue samples.

3. The storage device of claim 2, wherein said sample mounting elements are wells for holding a plurality of microscope glass slides, graticule slides, plastic slides or metal slides.

4. The storage device of claim 1, wherein said one-way hydrophobic membrane is formed from a material selected from the group consisting of polyethersulfone, nylon, and polytetrafluoroethylene.

5. The storage device of claim 1, further comprising an environmental sensing element for monitoring the environmental conditions within the interior of the storage device.

6. The storage device of claim 5, wherein said environmental sensing element is one selected from a hygrometer, a temperature sensor, a pressure sensor, a UV sensor, an accelerometer, or a combination thereof.

7. The storage device of claim 1, further comprising a sample identification element for identifying the samples stored therein.

8. The storage device of claim 7, wherein said sample identification element is selected from a surface area suitable for labeling with a marker, a sticker label, a barcode label, an RFID chip, or a combination thereof.

9. The storage device of claim 1, further comprising a time indicator for indicating a temporal information relating to the biological sample.

10. The storage device of claim 1, wherein said two housing portions comprise a top-half component and a bottom-half component, with the top-half component and the bottom-half component connected by a hinge.

11. The storage device of claim 1, wherein the desiccating cartridge attaches into the cartridge opening of the housing with a snap-fit.

12. The storage device of claim 1, wherein the desiccating cartridge is removable from the housing without opening the two housing portions with respect to each other.

13. The storage device of claim 1, wherein the desiccating cartridge comprises a one-way hydrophobic membrane.

14. The storage device of claim 13, wherein the one-way hydrophobic membrane is welded onto the cartridge after the cartridge is filled with desiccant.

15. A storage device for storing and preserving biological samples, comprising:
a housing comprising a bottom housing portion and a top housing portion which jointly define an interior space, the bottom housing portion having wells for holding a plurality of microscope glass slides, graticule slides, plastic slides or metal slides and thereby accommodate and secure therein a plurality of desiccated biological samples, the two housing portions being openable with respect to each other to permit access to the interior space, the two housing portions being closeable with respect to each other in a sealed fashion, the two housing portions being each formed of a material which is not permeable to air or moisture, one of the two housing portions in the closed state defining a cartridge opening;
a desiccating cartridge formed of a material which is not permeable to air or moisture, the desiccating cartridge being sized and shaped to fit and be removably received in the cartridge opening forming an air-tight fit with the housing so that, when the housing portions are in the closed state, the desiccating cartridge and the housing jointly seal the interior space of the housing off from the exterior environment, the desiccating cartridge having a compartment containing desiccant therein, the desiccating cartridge having one side facing the interior space through the cartridge opening which is permeable to air and moisture but not permeable to the desiccant; and a one way hydrophobic membrane disposed between the interior space and the desiccant when the cartridge is received in the cartridge opening and the housing portions are in the closed state.

16. The storage device of claim 15, wherein the top housing portion is hinged to the bottom housing portion.

17. The storage device of claim 16, wherein the desiccating cartridge attaches into the cartridge opening of the housing with a snap-fit.

18. The storage device of claim 17, wherein the cartridge opening is defined in the top housing portion.

19. The storage device of claim 18, wherein the desiccating cartridge is removable from the housing without opening the two housing portions with respect to each other.

20. The storage device of claim 19, wherein the one-way hydrophobic membrane is welded onto the cartridge after the cartridge is filled with desiccant.

21. The storage device of claim 20, wherein the one-way hydrophobic membrane is formed from a material selected from the group consisting of polyethersulfone, nylon, and polytetrafluoroethylene.

22. The storage device of claim 21, further comprising an o-ring to seal the top housing portion to the bottom housing portion.

23. The storage device of claim 22, wherein the top housing portion is locked to the bottom housing portion with clasps opposite the hinge.

* * * * *